US 7,223,418 B2

(12) United States Patent
Hidaka et al.

(10) Patent No.: US 7,223,418 B2
(45) Date of Patent: May 29, 2007

(54) STRETCHABLE PATCH

(75) Inventors: Osafumi Hidaka, Tokyo (JP); Akiko Ohata, Tokyo (JP)

(73) Assignee: Tiejin Limited, Osaka (JP)

( * ) Notice: Subject to any disclaimer, the term of this patent is extended or adjusted under 35 U.S.C. 154(b) by 6 days.

(21) Appl. No.: 09/959,420

(22) PCT Filed: Mar. 5, 2001

(86) PCT No.: PCT/JP01/01691

§ 371 (c)(1),
(2), (4) Date: Oct. 26, 2001

(87) PCT Pub. No.: WO01/66095

PCT Pub. Date: Sep. 13, 2001

(65) Prior Publication Data

US 2002/0146445 A1 Oct. 10, 2002

(30) Foreign Application Priority Data

Mar. 7, 2000  (JP) .............................. 2000-061676

(51) Int. Cl.
*A61F 2/00* (2006.01)
(52) U.S. Cl. ...................... 424/445; 424/400; 424/443; 424/447; 514/772; 514/772.3
(58) Field of Classification Search ............... 424/400, 424/402, 443
See application file for complete search history.

(56) References Cited

U.S. PATENT DOCUMENTS

| 5,298,258 A | | 3/1994 | Akemi et al. |
| 5,344,655 A | * | 9/1994 | Sakai et al. ............... 424/443 |
| 5,393,529 A | | 2/1995 | Hoffmann et al. |
| 5,753,256 A | | 5/1998 | Cordes et al. |
| 6,045,924 A | * | 4/2000 | Bekele ........................ 428/518 |
| 6,071,531 A | * | 6/2000 | Jona et al. .................. 424/449 |

FOREIGN PATENT DOCUMENTS

| EP | 0 900 565 A1 | | 3/1999 |
| EP | 0900565 | * | 10/1999 |
| JP | 10-226638 | | 8/1998 |
| WO | WO 97/23227 A1 | | 7/1997 |
| WO | WO 98/30210 | * | 7/1998 |

OTHER PUBLICATIONS

Kokubo, Takemasa, et al. "Diffusion of drug in acrylic-type pressure-sensitive adhesive matrices. I. Influence of physical property of the matrices on the drug diffusion", Journal of Controlled Release 17 Sep. 1991, No. 1, Amsterdam, NL.

* cited by examiner

*Primary Examiner*—Michael P. Woodward
*Assistant Examiner*—Eric E. Silverman
(74) *Attorney, Agent, or Firm*—Sughrue Mion, PLLC

(57) ABSTRACT

A stretch plaster comprising a support membrane having a thickness of 1 to 50 μm and a drug containing adhesive layer having a thickness of 3 to 400 μm, wherein
(i) the support membrane comprising a copolymer of 0 to 90% by weight of vinyl acetate, 10 to 97% by weight of alkyl (meth)acrylate having 3 to 14 of a mean carbon number of alkyl group and 0 to 15% by weight of (meth) acrylic acid,
(ii) the copolymer is cross-linked by polyvalent metal such as aluminum or a poly-functional chain compound, wherein the cross-linking ratio is 20% or more of the theoretical total number of carboxyl group of the copolymer when the polymer is cross-linked by the polyvalent metal such as aluminum, and is 1 to 10% expressed by copolymerized ratio of the poly-functional chain compound when the copolymer is cross-linked by poly-functional chain compound,
(iii) the support membrane has 150 g or less of self adhesion shown by an adhesion between the support membranes and
(iv) the support membrane has 70% or more of an elasticity recovery when it stretches 10% of itself.

7 Claims, No Drawings

STRETCHABLE PATCH

TECHNICAL FIELD

This invention relates to an excellent stretchable plaster. More particularly, this invention relates to a plaster comprising an adhesive layer including an adhesive substance formed on a flexible support that is stretchable. The plaster has no discomfort, less skin irritation and particularly fewer inconveniences such as peeling from the skin, even when the plaster is applied to body parts that are stretchable by body movement, for example, such parts as elbows or knees.

Percutaneous drug administration is a route of drug administration other than by oral administration or injection, etc. In percutaneous drug administration, patients can administer drugs by themselves and drug concentrations in the body (plasma drug concentration) can be kept constant. Moreover, percutaneous drug administration is suitable for topical diseases such as skin inflammation.

The plaster is one device that is widely used for percutaneous drug administration. With a plaster it is possible to attain constant administration of a drug and administration of drugs is simple.

A plaster has advantages over other devices for percutaneous administration. On the other hand, a disadvantage of the plaster, is skin irritation on body parts where it is applied, discomfort, difficult application, it easily peels from stretchable parts such as elbows or knees and the plaster has to be adhered on skin under clothes in order to conceal it.

To overcome these disadvantages, many ideas have been proposed. However, the first requirement of a plaster is transdermal permeation of drugs. Therefore, after the first requirement is satisfied, these disadvantages of the plaster have to be decreased.

Since the above-mentioned disadvantages are mutually interrelated, it is not an easy task to solve all the problems at one time.

For example, it is well known that skin irritation is caused by damping that occurs after excessive occlusion of the skin or by physical stimulation from hardness of the plaster, etc. Further, an excessively strong adhesion can become a cause of skin irritation or discomfort. However, in case where occlusion is not sufficient, transdermal permeation of drugs becomes inadequate and, therefore, it becomes necessary to increase the area of the plaster; this in turn, increases skin irritation and worsens handling of the plaster.

In addition, when hardness of the plaster is lowered, handling of the plaster becomes worse also. On the other hand, as hardness of the plaster is made higher, handling of the plaster becomes easier but skin irritation increases.

In the ordinary skill of the art of drug design, the properties desired by patients take precedence over other properties, and those other properties are compromised in permissible ranges.

For example, in case of tape formulations or plasters for anti-phlogistic agents, there are many formulations in which; a web comprising a stretch material such as urethane is used as a support in order to move together with the stretch of elbows and knees where inflammation is easy to occur. In order to increase the handlability of the plaster, etc., the thickness of support and drug containing adhesive layer is made large, hence, the plaster tends to be more stiff. In addition, adhesion of plasters, etc., are fixed as a low rate to prevent an ache at removing plasters, etc.

However these tape formulations and plasters for anti-phlogistic agents have a problem of peeling easily. Generally, at the time of using these plasters, peeling of the plaster is prevented by means of covering with a net or s bandage over the plaster. In addition, the plaster is changed as often as it peels.

There are many ordinary skills concerning these stretchable supports. However, a plaster satisfying both skin permeation of the drug, which is the primary object of the plaster and eliminating ordinary disadvantages is desired.

DISCLOSURE OF INVENTION

The object of this invention is to provide a plaster having sufficient percutaneous absorption of a drug, no discomfort even when it is applied on stretchable body parts such as elbows or knees, adherence stability even without a supporting net, and no pain at removal from parts of body to which it is adhered.

Further the object of the present invention is to provide a plaster having particularly low skin irritation and less prominence.

The inventors of this invention have achieved the present invention as a result of their earnest study based on a motivation making a plaster comprising safety adhesives.

Namely, this invention provides a stretch plaster comprising a support membrane having a thickness of 1 to 50 μm and a drug containing adhesive layer having a thickness of 3 to 400 μm, wherein (i) the support membrane comprising a copolymer of 0 to 90% by weight of vinyl acetate, 10 to 97% by weight of alkyl(meth)acrylate having 3 to 14 of a mean carbon number of alkyl group and 0 to 15% by weight of (meth)acrylic acid, (ii) the copolymer is cross-linked by polyvalent metal such as aluminum or a poly-functional chain compound, wherein the cross-linking ratio is 20% or more of the theoretical values of total number of moles of carboxyl group of the copolymer when the polymer is cross-linked by the polyvalent metal such as aluminum, and is 1 to 10% expressed by copolymerization ratio of the poly-functional chain compound when the copolymer is cross-linked by poly-functional chain compound, (iii) the support membrane has 150 g or less of self adhesion shown by an adhesion between the support membranes and (iv) the support membrane has 70% or more of an elasticity recovery when it stretches 10% of itself.

BEST MODE FOR CARRYING OUT THE INVENTION

The support membrane of the present invention includes a copolymerized copolymer that comprises 0 to 90% by weight of vinyl acetate, 10 to 97% by weight of (meth) acrylate alkyl ester having 4 to 14 of average carbon numbers and 0 to 15% by weight of (meth)acrylic acid.

Hereinafter in the present invention, the copolymer which has no vinyl acetate is sometimes described as acrylic based copolymer and the copolymer which has vinyl acetate is sometimes described as vinyl acetate-acrylic based copolymer.

The acrylic based copolymer includes, for example, a copolymer comprising (meth)acrylate alkyl ester and (meth) acrylic acid. The vinyl acetate-acrylic based copolymer includes, for example, a copolymer comprising vinyl acetate, (meth)acrylate alkyl ester and (meth)acrylic acid; a copolymer comprising vinyl acetate, (meth)acrylate alkyl ester, (meth)acrylic acid and vinyl ether such as vinyl butyl ether. Further the (meth)acrylate alkyl ester includes, for example, butyl(meth)acrylate, amyl(meth)acrylate, hexyl (meth)acrylate, heptyl(meth)acrylate, octyl(meth)acrylate, nonyl(meth)acrylate, decyl(meth)acrylate and 2-ethyl hexyl (meth)acrylate. In the present invention, when an acrylic based copolymer such as a copolymer of (meth)acrylate alkyl ester and (meth)acrylic acid is used, such (meth)acrylic acid is copolymerized 1 to 10 weight percent in advance in this acrylic based copolymer; and cross-linking of the acrylic based copolymer is carried out by either addition of polyvalent metal compounds or addition of 1 to 10 weight percent of poly-functional chain compounds at stage before the manufacture of the support membrane by coating. The polyvalent metal compound includes, for example, aluminum acetyl acetonate. The poly-functional chain compound includes, for example, 1,14-diglycidil ether.

In addition, in the case of using the acrylic based copolymer, the cross-linking ratio by using the polyvalent metal compound presents over 20% of ideal total molecular number of carboxylic base included in the acrylic based copolymer. It is preferable that the cross-linking ratio, which is shown by a polymerization ratio, is 1 to 10% when the poly-functional chain compound is used.

Generally, the adhesion of copolymer comprising (meth)acrylate alkyl ester and (meth)acrylic acid is strong. When a copolymer, which is commonly used as an adhesive, is applied for a support membrane, a high cross-linking ratio is needed. However, the polymer tends to harden due to the high cross-linking ratio.

In view of the above, preferable copolymer in the present invention is vinyl acetate-acrylic based copolymer comprising vinyl acetate, (meth)acrylate alkyl ester and (meth)acrylic acid.

It is preferable to obtain the object of the present invention that the adhesion of the above-mentioned vinyl acetate-acrylic based copolymer obtained by copolymerization with vinyl acetate, is weaker, and the adhesion strength of the membrane is higher.

Preferable content of the vinyl acetate-acrylic based copolymer includes 25 to 85% by weight of vinyl acetate, 10 to 60% by weight of (meth)acrylate alkyl ester and 1 to 10% by weight of (meth)acrylic acid. Especially preferable content is 50 to 85% by weight of vinyl acetate, 10 to 40% by weight of (meth)acrylate alkyl ester and 1 to 10% by weight of (meth)acrylic acid.

Examples of the especially preferable (meth)acrylate alkyl ester include octyl(meth)acrylate and 2-ethyl hexyl (meth)acrylate. In addition, even when a vinyl acetate-acrylic based copolymer, (meth)acrylic acid is copolymerized 1 to 10 weight percent in advance in this vinyl acetate-acrylic based copolymer; and cross-linking of the acrylic based copolymer is possible to carry out by either addition of polyvalent metal compounds or the addition of 1 to 10 weight percent of poly-functional chain compounds at a stage before the manufacture of the support membrane by coating.

An example of the polyvalent metal compounds includes aluminum acetyl acetonate. An example of a poly-functional chain compound includes 1,14-diglycidyl ether, etc.

The cross-linking ratio is 20% or more of the theoretical total number of moles of carboxyl groups in the vinyl acetate-acrylic based copolymer when the polymer is cross-linked by the polyvalent metal. When the polymer is cross-linked by a poly-functional chain compound, it is preferable to make the cross-linking ratio, which is shown by copolymerization ratio of the poly-functional chain coupound, 1 to 10%.

Especially, the vinyl acetate-acrylic based copolymer has a benefit that few gel-forming phenomena by cross-linking presents and coating for the copolymer can be carried out smoothly when polyvalent metal compounds such as aluminum acetyl acetonate are used.

The copolymers of the present invention, whether they are acrylic base copolymer or vinyl acetate-acrylic copolymers, can be polymerized or added with other polymerizable compounds as needed.

In this invention, problems such as sticking of a support membrane of the plaster with other parts of the support after being pressed together may occur, when the plaster is applied on to a stretchable body part (a crook) especially, such as elbows or knees because the polymer usable as the adhesive is generally adapted to the support membrane.

The inventors of the present invention have discovered that it is necessary to lower adhesion between the support membranes, namely self-adhesion, to solve the above-mentioned problem.

Concretely, preferable self-adhesion is 150 g or less for the present invention. The adhesion of conventional adhesive layers for medical plasters is over 150 g. Even minimum adhesion is 40 g or more.

However, the adhesion between the adhesive layers namely self-adhesion, is much stronger than 150 g. In many cases, the adhesion between the adhesive layers is 300 g or more, and it is strong enough to prevent separation. In the aforementioned uncross-linked state of the adhesive, the adhesion between the adhesive layers is 300 g or more. Therefore, the cross-linking ratio of the support membrane is fixed to achieve 150 g or less of the self-adhesion.

The adhesion of this invention is measured according to the test method specified in "Plaster" of the Japanese Pharmacopoeia. Adhesion between the adhesive layers (self-adhesion) is also measured according to this test. Adhesion of the plaster is measured by adhering a sample to a phenol resin plate. However, in case of measuring the adhesion between the adhesive layers (the self adhesion), it is measured by adhering between the support membranes.

In the present invention, a polymer (adhesive polymer) used as a conventional adhesive is applied to the support membrane. Therefore the plaster of the present invention can be stretched by moving of the skin, is not destroyed under using and has no peeling. On the other hand, toughness of the membrane tends to be small, because it is a usual physical property of adhesives and thickness of the membrane is small. Therefore, problems, in which the plaster is impossible to remove from the skin once it was applied may occur. To solve this problem, the proper strength is needed.

The present inventors found that the preferable strength of the support membrane of the present invention is 40 g or more when it is tested according the testing method specified in "Plaster of the Japanese Pharmacopoeia.

In order to obtain a support membrane that has a strength of 4 g or more, it is preferable that a vinyl acetate-acrylic based copolymer containing a vinyl acetate is selected and the copolymer is cross-linked.

Additionally, 350,000 or more of average molecular weight of the vinyl acetate-acrylic based copolymer is preferable. 450,000 or more average molecular weight is more preferable.

Further in view of less skin irritation, less prominence and less discomfort, a thin support membrane is preferable. The thickness of the support membrane is 1 to 50 μm, especially 5 to 30 μm of thickness is more preferable.

In the support membrane of the present invention, an elasticity recovery is needed to fix stably and comfortably on body parts stretching heavily such as elbows or knees. Concretely, the elasticity recovery is needed so that when the support membrane stretches 10% of itself (10% of stretch corresponds to a skin stretch in daily life), it recovers 70% of its stretched parts. When the elasticity recovery is low, some problems may occur. These problems are that the plaster peels, the plaster removes and the plaster is prominent on the skin.

In order to improve handling of the plaster, a cover layer can be laminated onto the side opposite of the drug containing adhesive layer of the plaster comprising the support membrane and the drug containing adhesive layer in the present invention.

In this case, the cover layer should have 50 g or less of adhesion with the support membrane.

The cover layer includes; a separate liner film comprising polyester, polyethylene, polypropylene, vinyl chloride or polyethylene vinyl acetate; a separate liner paper; a web comprising polyester, nylon, urethane, or silicon having 5 to 300 g/m² unit area weight; a knitted fabric; a woven fabric; or a non-woven fabric.

The thickness of the cover layer is 10 to 100 μm preferably.

In addition, the cover layer can be laminated the support membrane and cut into the same area size of the support membrane. When a part of the cover layer such as a vertical part or a horizontal part is 3 to 20 mm bigger than the support membrane, the handling of the plaster can be improved. When length and breadth of the cover layer is 3 to 20 mm bigger than the support membrane, also the handling of the plaster can be improved.

The plaster of the present invention can be attached with a separate liner (liner sheet) on a surface of the drug containing adhesive layer.

In the case where the cover layer is cut to have the same area size of the support membrane, a splitting cut line is formed on the center (10 to 90% area of vertical direction) of the cover layer. Therefore, only the liner can be removed first, during application. On the other hand, when a part of the cover layer is bigger than the support membrane, the split line may not be needed.

Moreover the cover layer can cover the entire support membrane or can be formed on a part of the support membrane so that the support membrane does not curl.

The cover layer can be formed after the plaster was manufactured or the cover layer can be formed by coating with a polymer in the process of manufacturing of the plaster.

Concretely, the support membrane in proper thickness is formed on the cover layer by coating with a solution such as the acrylic based copolymer comprising (meth)acrylate alkyl ester and (meth)acrylic acid; the vinyl acetate-acrylic based copolymer comprising vinyl acetate, (meth)acrylate alkyl ester and (meth)acrylic acid; and the vinyl acetate-acrylic based copolymer comprising vinyl acetate, (meth) acrylate alkyl ester and (meth)acrylic acid and vinyl ether comprising butyl vinyl ether. A combination of the cover layer and the support membrane, which has more uniformity and high stability, can be made by the above-mentioned method.

When a web is used as the cover layer, it is effective to laminate the web with the support membrane and then the resultant laminate is heated at 50 to 130° C. and pressed.

The drug containing adhesive layer of the present invention comprises the same adhesives as the support membrane, essentially. Also the drug containing adhesive layer can be added to other components.

The purpose of the drug containing adhesive layer is to fix the plaster of the present invention and to allow for absorption of the drug percutaneously.

The support membrane of the present invention fills a role of covering the drug containing adhesive layer and the other components of the plaster or other composite parts as a cover membrane of the plaster. On the other hand, the required property of the drug containing adhesive layer is different from that of the support membrane, therefore the drug containing adhesive layer has no limitation such as the strength of the self-adhesion.

The adhesives of the drug containing adhesive layer include a vinyl acetate based adhesive (EV) comprising 25 to 85% by weight of vinyl acetate, 10 to 60% by weight of alkyl(meth)acrylic acid having 3 to 14 of a mean carbon number and 1 to 10% by weight of (meth)acrylic acid; an acrylic based adhesive (AP) comprising 50 to 97% by weight of (meth)acrylate alkyl ester and 1 to 10% by weight of (meth)acrylic acid; and a mixture of EV and AP based adhesive. Especially EV is a preferable component, because EV is easily miscible with the drug generally, is highly safe to the skin and has a low adhesion. A preferable ratio of EV to AP in the mixture of EV and AP is 0.1 to 20.

The alkyl(meth)acrylic acid having 3 to 14 of a mean carbon number includes, for example, butyl(meth)acrylate, amyl(meth)acrylate, hexyl(meth)acrylate, octyl(meth)acrylate, nonyl(meth)acrylate, decyl(meth)acrylate and 2-ethyl hexyl(meth)acrylate.

The adhesive of the drug containing adhesive layer is not required to have the same components as the support membrane. Adhesives such as an ordinary acrylic based, a rubber based, a silicon based or a vinyl acetate based adhesives can be employed.

Since the objectives in this invention are less skin irritation, less discomfort and less ache under peeling, a low adhesion of the drug containing adhesive layer is preferable. The adhesion of conventional plasters is more than 150 g, as specified in "Plaster" in the Japanese Pharmacopoeia. This value is needed to prevent peeling of the plaster from the skin. The plaster of the present invention is not easy to peel, because the stretch support membrane is employed. To prevent an ache from peeling, a preferable adhesion of the present plaster is 150 g or less, more preferably 30 to 120 g.

However the adhesion to the skin depends on the duration of administration, and the adhesion of "Plaster" described in the Japanese Pharmacopoeia is a value of adhesion to a phenol resin board. Therefore we don't need to stickle about the value mentioned above.

The adhesion of the present plaster to the skin can be smaller than that of the ordinary plaster. Though the present plaster can prevent the ache of patients under peeling, the present plaster is harder to peel off than the ordinary plaster.

The drug in the present invention includes antiphlogistic agent such as salicylate esters, indomethacin and ketoprofen, hormones for dermatosis such as valeric acid, betamethasone and dexamethasone, vitamins such as vitamin A, vitamin C and vitamin E, coronary vasodilators such as isosorbide nitrate and nitroglycerin, sedative drugs/anxiolytics such as brotizelam and triazolam, anti-hypertensives/circulatory agents such as propranolol, antibiotics, anti-tussives/bronchodilators such as tulobuterol hydrochloride, ambroxol hydrochloride, ipratropium bromide, tranilast, azerastine hydrochloride and clenbuterol hydrochloride, anti-ulcer agents such as clebopride malate, famotidine and lansoprasole, hormones such as estradiol, anti-allergic agents such as feroxy phenazine and anti-psoriasis agents such as tacalcitol. However the drug of the present invention is not limited to these drugs mentioned above.

Further components except the aforementioned medical drug can be used for beauty, health and moisturizer products. Examples of these components include urea, liquid paraffin, polyethylene glycol, glycerin, propylene glycol, surfactants, squalene, cayenne pepper, extract from natural products such as herb, zinc oxide, titanium oxide, living rock, rock having far-infrared ray, ceramic, silk fiber or their component.

The plaster of this invention has extremely low discomfort, so the plaster can be adhered stably on crooks such as elbows or knees. Additionally the plaster is not prominent on the skin. Therefore the plaster has benefits in the object of beauty, health and moisturize. And ordinary plasters have never had these benefits.

In the present plaster, the volume of drugs and the ratio of drugs are extremely flexible. In many cases with conventional plasters, to achieve high percutaneous absorption of drug, the drug concentration of the plaster is high and the third component is added. Therefore the adhesion of the adhesive layer becomes low, so the volume or ratio of the third component is limited. However in the plaster of the present invention, adhesion to the skin is comparatively low, so the volume of drugs and the ratio of drugs are extremely flexible.

Generally, the volume of the drug of plasters is 0.01 to 30% by concentration of the adhesive. But, for example, in case of tacalcitol, plasters having 0.0001 to 0.01% of tacalcitol have pharmacological effects, therefore the drug concentration can be fixed by drug effect of active component and indication of drug.

In percutaneous absorption, the drug can be prevented from the first pass effect, so the drug content which can show the drug effect is known as same content or ¹⁄₁₀₀ compared to administration routes such as by oral administration. However, the ratio of percutaneous absorption is influenced by the drug concentration in the adhesive layer and a drug concentration gradient in the skin, which is a role for serving as a barrier to drug permeation. Hence, it is said that the drug content in pharmaceutical compositions is required to be the same amount or 1000 times the amount of the drug absorbed into the body.

Namely, the range of the absolute bioavailability (BA) by percutaneous absorption is 0.1 to 100%, actually it is 0.1 to 50%, and generally, in consideration of these values, drug content and concentration in pharmaceutical compositions is determined.

It is possible to set the drug containing adhesive layer in the present invention at 3 to 400 μm in thickness.

Generally, the adhesion of plasters is stronger according to thickness of the drug containing adhesive layer. From the view of adhesion, preferable thickness of the adhesive layer is 10 μm or more, and 30 μm or more ordinary. However in the present invention, it is possible that the thickness of adhesive layer is set at less than ordinary ones, because it is allowed to make the adhesion to the skin to remain low. Additionally, a maximum of preferable thickness is 100 μm or 200 μm in ordinary plaster, however, the present plaster can keep its ability as a pharmaceutical product, even the drug containing adhesive layer is thicker than the ordinary, because the supporter of the present invention is thin. A more preferable thickness of the drug containing adhesive layer in this invention is 5 to 200 μm.

In the present plaster, for improvement of the hardness under administration, for beauty or for increasing of drug permeation to the skin, it is possible to divide the drug containing adhesive layer itself or an inside thereof, into several parts. On the other hand, it is possible to imbed other components of plasters, making the plaster a multi-laminated layer, by burying another base as a lamination layer.

EXAMPLES

Following examples illustrate the present invention. However, it should not be understood that these examples are given to limit the scope of the invention. In these examples, parts, % and ratio are shown by weight.

The following is one of the synthetic vinylacetate based adhesives (EV-51) used in these examples.

70% of vinyl acetate, 27.5 parts of 2-ethyl hexyl acrylate, 2.5 parts of acrylic acid, 1.0 parts of benzoyl peroxide and 200 parts of ethyl acetate are set in the reaction vessel with a reflux condenser and mixer. They are polymerized by gradually mixing for 18 hours under $N_2$ gas at 60° C. The resultant vinyl-acetate based copolymer had a molecular weight of 650,000. The concentration of the solution is prepared to be 30% by addition of ethyl acetate.

Also the following is one synthetic acrylic based (AP-52) adhesive used in the examples.

90 parts of 2-ethylhexyl acrylate, 7.5 parts of methyl methacrylic acid, 2.5 parts of acrylic acid, 1.0 part of benzyl peroxide and 300 parts of ethyl acetate acid as set in the reaction vessel with a reflux condenser and mixture. Then polymer is produced by gently mixing for 17 hours under $N_2$ gas at 60° C. The obtained acrylic based copolymer had a mean molecular weight of 580,000. The concentration of the polymer mixture was prepared to be 20% by addition of ethyl acetate.

Example 1

<Preparation of the Support Membrane>

100 parts of 30% ethyl acetate solution of vinyl acetate based adhesive (EV-51) was added to 0.675 parts of aluminum acetyl acetate was dissolved in 12 parts of acetyl acetone, and then mixed well. The resultant solution was coated on 75 μm thickness of polyethylene terephthalate liner to be 10 μm thick after drying. After drying for 1 minute at 70° C., for 1 minute at 80° C. and for 1 minute at 120° C., the obtained 10 μm thickness of the support membrane is coated with a 75 μm thick polyethylene terephthalate liner.

In this case the cross-linking ratio of EV-51 was 60%. It was calculated on the supposition that one mole of trivalent of aluminum bind to 3 moles of carboxyl group.

The strength of obtained support membrane with liner was 12 g.

<Preparation of a Drug Containing Adhesive Layer>

233 parts of 30% EV-51 ethyl acetate solution, 175 parts of AP-52 ethyl acetate solution, 30 parts of isopropyl myristate and 0.263 parts of indomethacin are well mixed. Then the solution is coated on the another 75 μm thickness of polyethylene terephtalate liner, and dried for 2 minutes at 70° C., for 2 hours at 80° C. and for 2 minutes at 110° C. to obtain the 100 μm thick drug containing adhesive layer.

The adhesion of the obtained adhesive layer was 25 g.

The resultant adhesive layer with a liner is laminated on the surface of the support membrane with the liner. Then it is cut out into a rectangle shape with the 100 mm×70 mm size. Subsequently, splitting cut line is formed on the surface of the liner that is adhered on one side of the adhesive layer, and the indomethacin containing plaster was obtained.

The indomethacin containing plaster is cut at 1.13 cm² of area and adhered on a back of the hairless rat whose hair was shaved for 21 hours, and then the amount of drug absorption was determined; the amount of drug absorption was about 10% and the amount of drug absorbed was equivalent to commercially available indomethacin plaster. Under adhering of the plaster in this test, the protecting material was not required. On the other hand, the commercial plaster was required by the protection with gauze.

The removal strength between the support membranes of a commercial indomethacin plaster was 23 g.

Experiments 1 to 6

In the preparation of the support membrane, several of support membranes which have various cross-linking ratios were produced by changing the content of aluminum acetyl acetonate in the comparison of example 1. Table 1 shows their cross-linking ratio and removal strength.

Experiment 7

To investigate the feeling of plaster during use of the present invention, placebo plasters, which do not contain indomethacin, were manufactured according to example 1. 100 mm×70 mm area of the placebo plasters were adhered on human elbows for 24 hours. (n=3) While adhering, there was no peeling off of plasters, they felt a little uncomfortable, and when removing, it was confirmed that they felt no aches and the support membrane kept good shape.

Comparative Example 1

According to example 1, the indomethacin containing plaster was manufactured except aluminum acetyl acetonate in the preparation steps of the support membrane. When the product was adhered to rat, it was difficult because of adhesion of the support membrane. In this case the removal strength between the support membranes (self-adhesion) was 500 g or more.

Experiment 8

To investigate the feeling during use while adhering the plaster, the placebo plasters according to example 1 except indomethacin were manufactured at the area of 100 mm×70 mm. An adhering test of the placebo plaster on a human elbow for 24 hours was planned. However the placebo plasters could not be adhered to the human elbow, because the adhesion of the support membrane caused adhesion between the support membranes and the placebo plaster could not keep its shape for adhering at human elbows.

TABLE 1

Cross-linking ratio and peeling strength between the support membranes (self-adhesion)

| Cross-linking ratio (%) | Self-adhesion (g) |
| --- | --- |
| 6 | 500 or more |
| 10 | 370 |
| 20 | 131 |
| 40 | 62 |
| 60 | 12 |
| 100 | 6 |

The invention claimed is:

1. A stretch plaster comprising a support membrane having a thickness of 3 to 30 μm and a drug containing adhesive layer on one side thereof, said adhesive layer having a thickness of 3 to 400 μm, wherein
   (i) the support membrane comprises a copolymer consisting essentially of 50 to 85% by weight of vinyl acetate, 10 to 40% by weight of a (meth)acrylate alkyl ester, wherein the alkyl group has 3 to 14 carbon atoms and 1 to 10% by weight of (meth)acrylic acid,
   (ii) the copolymer is cross-linked by a polyvalent metal selected from the group consisting of aluminum and a poly-functional chain compound, wherein the cross-linking ratio is 20% or more of the total molar number of carboxyl group of the copolymer when the polymer is cross-linked by aluminum, and is 1 to 10% expressed by copolymerized ratio of the poly-functional chain compound when the copolymer is cross-linked by a poly-functional chain compound,
   (iii) the support membrane has a self adhesion strength of 150 g or less and
   (iv) the support membrane has 70% or more of an elasticity recovery when it stretches 10% of itself and,
   (v) the support membrane does not contain a drug.

2. The stretch plaster according to claim 1, wherein the drug containing adhesive layer has a thickness of 5 to 200 μm.

3. The stretch plaster according to claim 2, wherein the copolymer is a vinyl acetate-acrylic based copolymer cross-linked by aluminum, wherein the cross-linking ratio is 20% or more of the total molar number of carboxyl groups of the copolymer, and the support membrane has a self adhesion strength of 100 g or less.

4. The stretch plaster according to claim 1, wherein the support membrane has a cover layer on the opposite side of the drug containing adhesive layer for improvement of its handling, and has a self adhesion strength of 50 g or less.

5. The stretch plaster according to any one of claims 1 to 4, wherein the drug is selected from the group consisting of antiphlogistic agents, hormones for dermatosis, vitamins, coronary vasodilators, sedative drugs, anxiolytics, anti-hypertensives, circulatory agents, antibiotics, anti-tussives, bronchodilators, anti-ulcer agents, hormones, anti-allergic agents and anti-psoriasis agents.

6. The stretch plaster according to claim 4, wherein the drug is selected from the group consisting of salicylate esters, indomethacin, ketoprofen, valeric acid, betamethasone, dexamethasone, vitamin A, vitamin C, vitamin E, isosorbide nitrate, nitroglycerin, brotizelam, triazolam, propranolol, tulobuterol hydrochloride, ambroxol hydrochloride, ipratropium bromide, tranilast, azerastine hydrochloride, clenbuterol hydrochloride, clebopride malate, famotidine, lansoprasole, estradiol, feroxy phenazine and tacalcitol.

7. The stretch plaster according to claim 1, wherein the plaster has an adhesion strength of 30 to 120 g.

* * * * *

UNITED STATES PATENT AND TRADEMARK OFFICE
CERTIFICATE OF CORRECTION

| | | |
|---|---|---|
| PATENT NO. | : 7,223,418 B2 | Page 1 of 1 |
| APPLICATION NO. | : 09/959420 | |
| DATED | : May 29, 2007 | |
| INVENTOR(S) | : Osafumi Hidaka and Akiko Ohata | |

It is certified that error appears in the above-identified patent and that said Letters Patent is hereby corrected as shown below:

Title Page
(73) Please delete "Assignee: Tiejin Limited, Osaka (JP)" and insert --Assignee: Teijin Limited, Osaka (JP)--

Signed and Sealed this

Sixteenth Day of October, 2007

JON W. DUDAS
*Director of the United States Patent and Trademark Office*